United States Patent [19]

Childers et al.

[11] Patent Number: 5,527,507
[45] Date of Patent: Jun. 18, 1996

[54] ACCUMULATOR BASED LIQUID METERING SYSTEM AND METHOD

[75] Inventors: Robert W. Childers, Garner; Columbus C. Cockerham, Jr., Apex; Matthew S. Dixon; Donald L. Eddington, both of Raleigh; Steve J. Edwards, Apex, all of N.C.

[73] Assignee: American Sterilizer Company, Erie, Pa.

[21] Appl. No.: 236,697

[22] Filed: May 2, 1994

Related U.S. Application Data

[63] Continuation of Ser. No. 955,301, Oct. 1, 1992, abandoned.

[51] Int. Cl.[6] .................................................. A61L 2/00
[52] U.S. Cl. ........................ 422/28; 422/33; 422/298
[58] Field of Search .......................... 422/26, 27, 28, 422/33, 39, 295, 298; 436/180; 137/209, 572, 575; 222/450

[56] References Cited

U.S. PATENT DOCUMENTS

| | | |
|---|---|---|
| H980 | 11/1991 | Harrison . |
| 2,007,738 | 7/1935 | Baer .......................................... 422/28 |
| 3,190,509 | 6/1965 | Kirchhoefer . |
| 3,597,934 | 8/1971 | Andersen ................................. 62/50.2 |
| 3,893,625 | 7/1975 | Wiggins . |
| 3,929,411 | 12/1975 | Takano et al. . |
| 4,398,852 | 8/1983 | Milligan . |
| 4,410,492 | 10/1983 | Kaye . |
| 4,731,222 | 3/1988 | Kralovic et al. . |
| 4,817,800 | 4/1989 | Williams et al. . |
| 4,869,286 | 9/1989 | Williams et al. . |
| 4,892,706 | 1/1990 | Kralovic et al. . |
| 4,899,519 | 2/1990 | Williams et al. . |
| 4,909,287 | 3/1990 | Williams et al. . |
| 4,909,999 | 3/1990 | Cummings et al. . |
| 4,913,196 | 4/1990 | Williams et al. . |
| 4,938,262 | 7/1990 | Williams et al. . |
| 4,941,518 | 7/1990 | Williams et al. . |
| 4,941,519 | 7/1990 | Sestak et al. . |
| 4,943,414 | 7/1990 | Jacobs et al. . |
| 4,952,370 | 8/1990 | Cummings et al. ....................... 422/28 |
| 4,956,156 | 9/1990 | Kanner et al. ........................... 422/300 |
| 4,973,449 | 11/1990 | Kolstad et al. . |
| 5,116,575 | 5/1992 | Badertscher et al. ..................... 422/28 |
| 5,122,344 | 6/1992 | Schmoegner . |
| 5,173,258 | 12/1992 | Childer . |
| 5,350,568 | 9/1994 | Tuckner et al. .......................... 422/300 |

FOREIGN PATENT DOCUMENTS

| | | |
|---|---|---|
| 2010779 | 4/1979 | United Kingdom . |
| 2052800 | 1/1981 | United Kingdom . |
| 2105591 | 3/1983 | United Kingdom . |
| 2127692 | 4/1984 | United Kingdom . |
| 2191585 | 3/1987 | United Kingdom . |

OTHER PUBLICATIONS

Tridak 1989 Product Literature.
TL Systems Product Literature.
Carvo Scientific Inst. Product Literature.

*Primary Examiner*—Robert J. Warden
*Assistant Examiner*—Robert Carpenter
*Attorney, Agent, or Firm*—Jones, Day, Reavis & Pogue

[57] ABSTRACT

A method for metering a liquid sterilant from a reservoir or other container into a vaporization system, in accurately and reproducibly measured amounts. The method includes the steps of delivering the liquid sterilant from the container into an accumulator, at a first delivery pressure and a first delivery rate, discontinuing the dispensing of liquid sterilant when a predetermined amount of sterilant has been transferred from the container into the accumulator, and delivering liquid sterilant from the accumulator into the vaporizer, at a second delivery pressure and a second delivery rate. The first delivery pressure and first delivery rate are preferably lower than the second delivery pressure and second delivery rate.

32 Claims, 5 Drawing Sheets

ACCUMULATOR BASED LIQUID METERING SYSTEM AND METHOD

This is a continuation of application Ser. No. 07/955,301 filed on Oct. 1, 1992, now abandoned.

FIELD OF THE INVENTION

The present invention relates to a method of metering a liquid, and more particularly to a method of metering a liquid from a reservoir or other container into a vaporization system. The vapor or gas produced by the vaporization system is typically used for sterilization/decontamination purposes.

BACKGROUND OF THE INVENTION

Generally, in vapor phase sterilization, a liquid sterilant is metered from a reservoir or other container into a vaporizer or sterilization chamber in which vaporization occurs. To ensure effective and efficient sterilization, the liquid should be metered in accurately and reproducibly measured amounts.

Several different methods have been proposed for metering liquid sterilant into a vaporization system. In one approach, a cassette having a group of sealed cells is coupled to a sterilization chamber by dispensing apparatus. Each cell contains a predetermined dose of liquid sterilant. After the sterilization chamber is evacuated, the cells are punctured sequentially, and their contents forced into the evacuated chamber by pneumatic pressure.

Because the amount of sterilant injected is limited to the cell volume, or multiples thereof, the foregoing approach is not flexible. It also is not practical or economical for use in multi-phase or flow-through sterilization cycles, which would require multiple cassettes. Further, shelf-life problems arise, for example, when the system is employed to dispense small amounts (e.g., a few mls) of hydrogen peroxide sterilant. During storage, the hydrogen peroxide is prone to degrade into gases or vapors, which may rupture the cassette cells, unless vented. Venting, however, reduces the sterilant concentration over time.

In other known proposals, a dispensing pump propels the liquid sterilant directly from a reservoir into a vaporizer, through dispensing lines. Liquid metering is accomplished by various known methods, including: a) controlling the volume dispensed per pump stroke; b) controlling the revolution rate of a continuous flow, fixed output pump; and c) controlling the dispensing time period from a continuous flow, fixed output pump. Alternatively, metering is achieved by mounting the liquid reservoir on an electronic balance, and then monitoring the weight loss as the liquid is pumped from the reservoir.

In a further approach, liquid sterilant is metered into the vaporizer by controlling the time period dispensing occurs at a fixed, controlled pressure or vacuum level. Again, the liquid sterilant is carried directly from the reservoir into the vaporizer, through dispensing lines.

The previously proposed pump/pressure dispensing methods may perform satisfactorily, within their given dispensing capabilities and accuracies, when the liquid does not degrade into or otherwise generate vapors or gases during storage or handling. However, when gases or vapors are produced from liquid retained in the dispensing equipment, the performances of such methods can be adversely affected.

For example, in the prior methods which meter by controlling operating parameters of a fixed rate, volumetric pump, entrained air bubbles (and other gases/vapors) prevent the sterilant liquid from being accurately and reproducibly metered, because the pump cannot distinguish between the liquid sterilant and air bubbles. Further, if equipment incorporating a stroke-type pump is allowed to sit idle for an extended period of time, air bubbles forming in the lines, valves, and filters may even prevent the pump from operating, i.e., the system will "vapor lock."

Similarly, air bubbles adversely affect the performance of methods which meter liquid sterilant by controlling the dispensing time period at a fixed pressure or vacuum, because the liquid is pushed or sucked into the vaporizer, along with the air bubbles, in a non-uniform matter.

Dispensing accuracy may also be reduced in systems which monitor weight loss from the liquid reservoir, when such systems sit idle for several hours. Weight loss from the reservoir, as measured by the balance, does not account for the air bubbles formed in the dispensing lines, which are dispensed into the vaporizer at start-up. To enhance dispensing accuracy, the dispensing lines can be purged prior to injection, to replace any remaining liquid having entrained air bubbles with substantially pure liquid. This has been accomplished by directing a high rate of liquid flow through the dispensing lines and back into the reservoir, with a diverter valve. This procedure does not entirely avoid measuring problems created by air bubbles, however, where the pump sucks entrained air bubbles back into the liquid reservoir and into the dispensing lines, during the purge step.

Metering problems caused by air bubbles are aggravated when the liquid sterilant is injected into the vaporizer in intermittent pulses, because the smaller increments injected require better resolution. Also, bubbles build-up between pulses and steady state conditions are not achieved.

Other problems are presented by the prior metering methods, which dispense liquid sterilant directly from the reservoir to the vaporizer. In general, when employing a sterilant such as hydrogen peroxide, which breaks down over time, high injection rates and pressures (or vacuums) are desired, to ensure that the sterilant is moved quickly through the vaporizer to the intended sterilization site. However, high dispensing pressures may also give rise to increased system leaks. The dispensing equipment must be constructed from materials which can physically withstand such high pressures and yet retain material compatibility with the liquid sterilant.

Further, the measuring resolution of the system is reduced at higher dispense rates and pressures. This problem is compounded when the increased liquid agitation which accompanies high delivery speeds and pressures generates additional air bubbles.

In the prior metering methods, if the pressure (or suction) or dispense rate is reduced to provide a lower liquid flow, in an attempt to increase metering resolution and reduce system leaks, the time period for injecting amounts of liquid into the vaporizer (and through to the sterilization chamber) is undesirably increased. Further, when liquid sterilant is metered by monitoring the dispensing time period at a fixed pressure or vacuum, it has been determined that the dispense rate fluctuates with the liquid sterilant level in the reservoir.

There is a need for a method of metering liquid sterilant from a reservoir into a vaporization system, in accurately and reproducibly measured amounts, particularly where the liquid vapor forms gases or vapors during storage and handling. There is also a need for a metering method which can deliver the measured liquid sterilant into the vaporizer at higher pressures and speeds, while avoiding system leaks and material compatibility problems.

SUMMARY OF THE INVENTION

The present invention provides a method of metering a liquid sterilant from a container, such as a reservoir, into a vaporization system, for vapor phase sterilization/decontamination, in accurately and reproducibly measured amounts. In accordance with the invention, liquid sterilant is first delivered or dispensed from the container into an accumulator, at a first delivery pressure and a first delivery rate. The delivery of liquid sterilant from the reservoir is discontinued after a pre-determined amount of sterilant has been transferred from the reservoir into the accumulator. Then, the amount of liquid sterilant delivered into the accumulator is discharged or injected into a vaporizer (or sterilization chamber, where vaporization occurs), at a second delivery pressure and a second delivery rate. The reservoir is fluidly coupled to the accumulator, and the accumulator is fluidly connected to the vaporizer, with fluid connecting means.

The amount of sterilant delivered from the reservoir into the accumulator is preferably determined by a measuring step which comprises weighing the amount of liquid removed from the reservoir (and delivered to the accumulator) with a balance positioned under the reservoir, or measuring the volume of liquid transferred into the accumulator with a level sensor or conductivity probe positioned at a predetermined level or levels inside the accumulator.

When greater or enhanced measuring resolution is desired, the method preferably also comprises the steps of purging substantially all liquid from the dispensing lines upstream of the accumulator with an air flow, after each measurement, and priming the lines with substantially pure liquid from the reservoir, at the beginning of the next measurement pulse.

The first delivery pressure and first delivery rate are preferably lower than the second delivery pressure and second delivery rate, respectively.

The invention also provides a system for metering a liquid sterilant from a container, such as a reservoir, into a vaporizer (or sterilization chamber, where vaporization occurs). The system includes a reservoir for the liquid sterilant, an accumulator for receiving liquid sterilant from the reservoir, a vaporizer for vaporizing the liquid sterilant, first delivery means for delivering the liquid sterilant from the reservoir into the accumulator, second delivery means for delivering the liquid sterilant from the accumulator into the vaporizer, and means for measuring the amount of liquid sterilant delivered from the reservoir into the accumulator.

BRIEF DESCRIPTION OF THE DRAWINGS

The present invention can best be understood by reference to the drawings, in which.

DETAILED DESCRIPTION OF THE INVENTION

Figure 1:
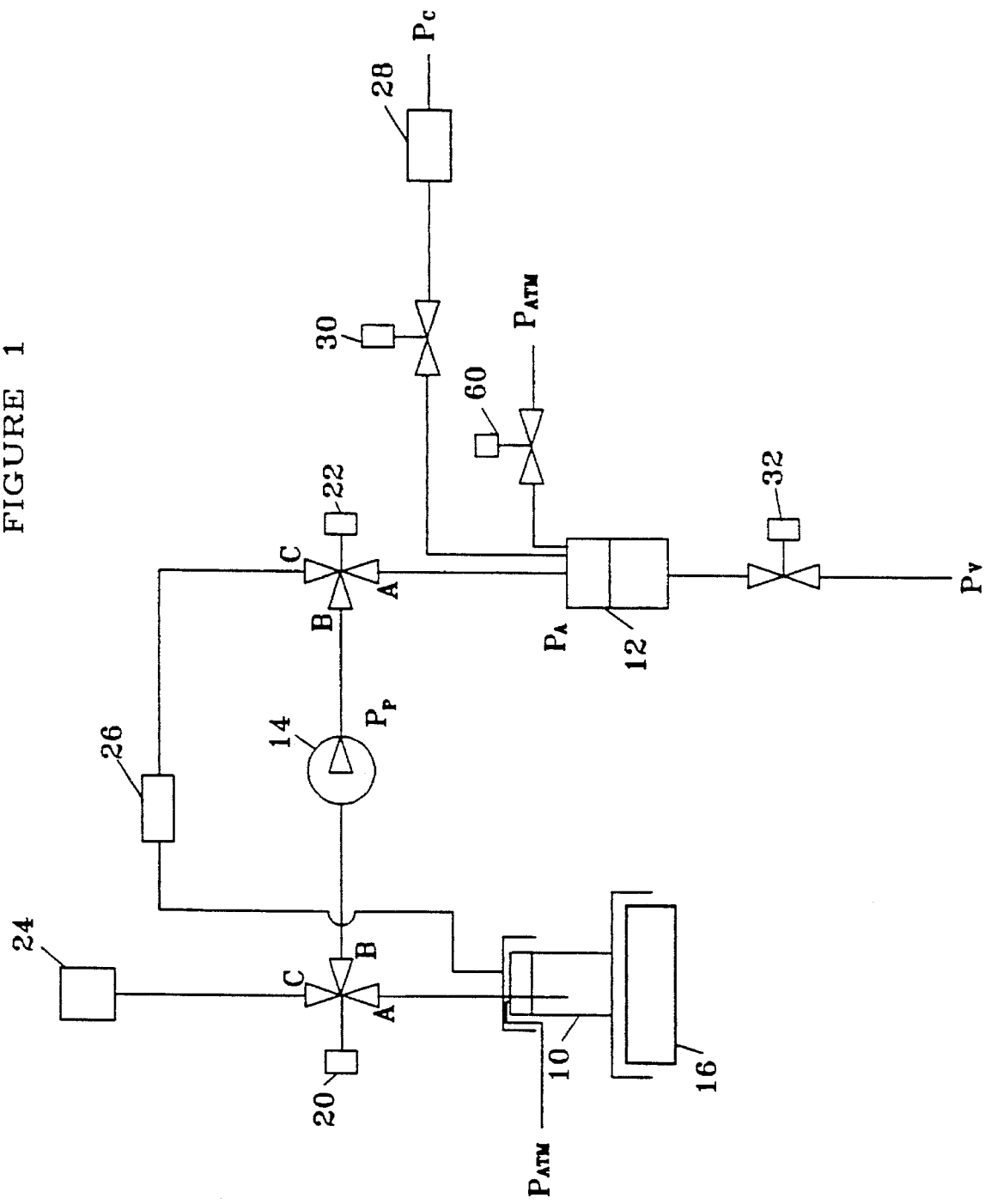
FIG. 1 is a schematic diagram of one embodiment of a system for practicing the method of the present invention, wherein an electronic balance for measuring the amount of liquid dispensed, on a weight basis, is employed.

The present invention provides a method and system for metering a liquid sterilant from a reservoir, or other container, into a vaporization system, in accurately and reproducibly measured amounts, for vapor phase decontamination/sterilization.

Rather than metering the liquid sterilant directly from the reservoir into a vaporization system, the method of the present invention divides the dispensing operation into two steps. First, an accumulator is filled with the desired amount of liquid sterilant from the reservoir. Second, the measured amount of liquid in the accumulator is discharged into a vaporizer.

In the vaporizer, the liquid sterilant is substantially vaporized and can then be drawn, in vapor form into a sterilization chamber or enclosure. The vaporized sterilant can be carried from the vaporizer to the sterilization chamber, for example, by creating a pressure differential (such as suction generated by evacuating the sterilization chamber) or by flowing the vaporized sterilant to the sterilization chamber with a carrier gas, under a pressure differential. Preferably, the liquid sterilant is delivered from the accumulator to the vaporizer, through an injection valve, in nearly continuous pulses or increments, such that there is substantially a steady stream of increments into and through the vaporizer to the sterilization chamber. (Alternatively, it is contemplated that the liquid sterilant can be delivered from the accumulator into a sterilization chamber, where vaporization occurs, i.e., a separate vaporizer is not used.)

Because the dispensing operation is split into two steps, the liquid sterilant can be delivered into the accumulator from the reservoir at a different pressure and rate than the pressure and rate at which the liquid sterilant is subsequently delivered into the vaporizer. Thus, the desired amount of liquid sterilant can always be slowly measured into the accumulator at low pressure, thereby increasing the measuring resolution, particularly when small amounts of liquid are desired.

Further, the accurately measured amount of liquid can be injected from the accumulator into the vaporizer, and through to the sterilization chamber, at virtually any desired speed and pressure. In the case of sterilant vapors, such as hydrogen peroxide, which are unstable, degrade, or otherwise become ineffective over time, high injection rates can be used to ensure that the vaporized sterilant is delivered and distributed quickly to the area or object of sterilization, and to maximize sterilization efficiency.

Because the liquid sterilant is delivered from the reservoir into the accumulator at low pressure, the components upstream of the accumulator, e.g., the accumulator fill piping, can be fabricated from materials, compatible with the liquid sterilant, which might not successfully withstand higher pressures. Thus, for example, where liquid hydrogen peroxide is employed, the components upstream of the accumulator can be manufactured from chemically inert plastics, such as polycarbonate or polyethylene, Teflon and Kynar, which might leak if exposed to high operating pressures.

Also, because the liquid sterilant is discharged quickly from the accumulator, the material compatability requirement of the accumulator is substantially reduced. Thus, the accumulator can be fabricated from stainless steel or other metals capable of withstanding high injection pressures but not storage stable with liquid hydrogen peroxide, for example. The short contact time between the accumulator and the liquid hydrogen peroxide preclude unacceptable decomposition of the liquid hydrogen peroxide.

The invention is particularly suited for use with liquid sterilants that degrade into or otherwise produce gases or vapors, such as air bubbles, during storage or handling. Preferably, the invention is practiced with an aqueous hydrogen peroxide solution, and more preferably with a 30–35 percent (by weight) aqueous hydrogen peroxide solution. In practicing the invention with hydrogen peroxide solutions, all air entering the system is preferably HEPA filtered, to remove any particles which might catalytically or otherwise destroy the sterilant. It is contemplated that other volatile liquids, such as peracetic acid, may also be used.

It is also contemplated that the invention can be used in connection with any known sterilization cycle. The invention is particularly suited for use with a sterilization cycle employing intermittent, pulsed injections of sterilant vapor through the vaporizer into the sterilization chamber, particularly when there is a gap of more than one minute between the series of pulses, during which the accumulator can be slowly refilled with liquid sterilant.

The invention will now be described with reference to FIGS. 1–3, which illustrate preferred embodiments. The metering system includes a reservoir 10, filled with liquid sterilant and fluidly coupled via suitable conduit to an accumulator 12. A metering pump 14, which is preferably a peristaltic tubing pump, is fluidly connected to the fluid connection between the reservoir 10 and accumulator 12. The accumulator 12 is fluidly connected via suitable conduit to a vaporizer (not shown), located downstream of the accumulator. The fluid connection to the vaporizer is at pressure $P_V$ so that a pressure differential exists whenever the accumulator pressure $P_A$ is greater than the vaporizer conduit pressure $P_V$.

Figure 2:
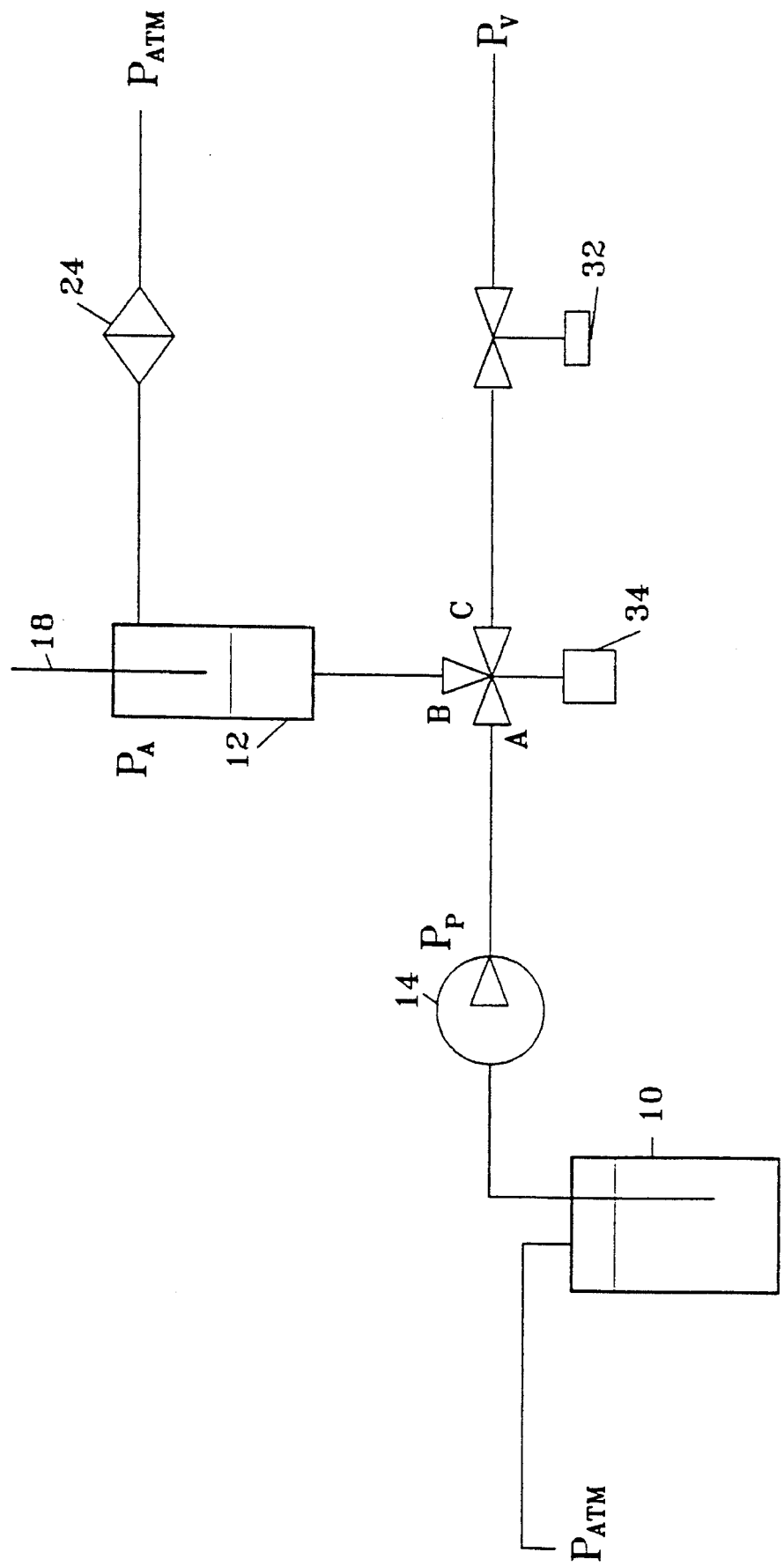
FIG. 2 is a schematic diagram of a second embodiment of a system for practicing the method of the present invention, wherein a conductivity probe for measuring the amount of liquid dispensed, on a volumetric basis, is employed.
Figure 3:
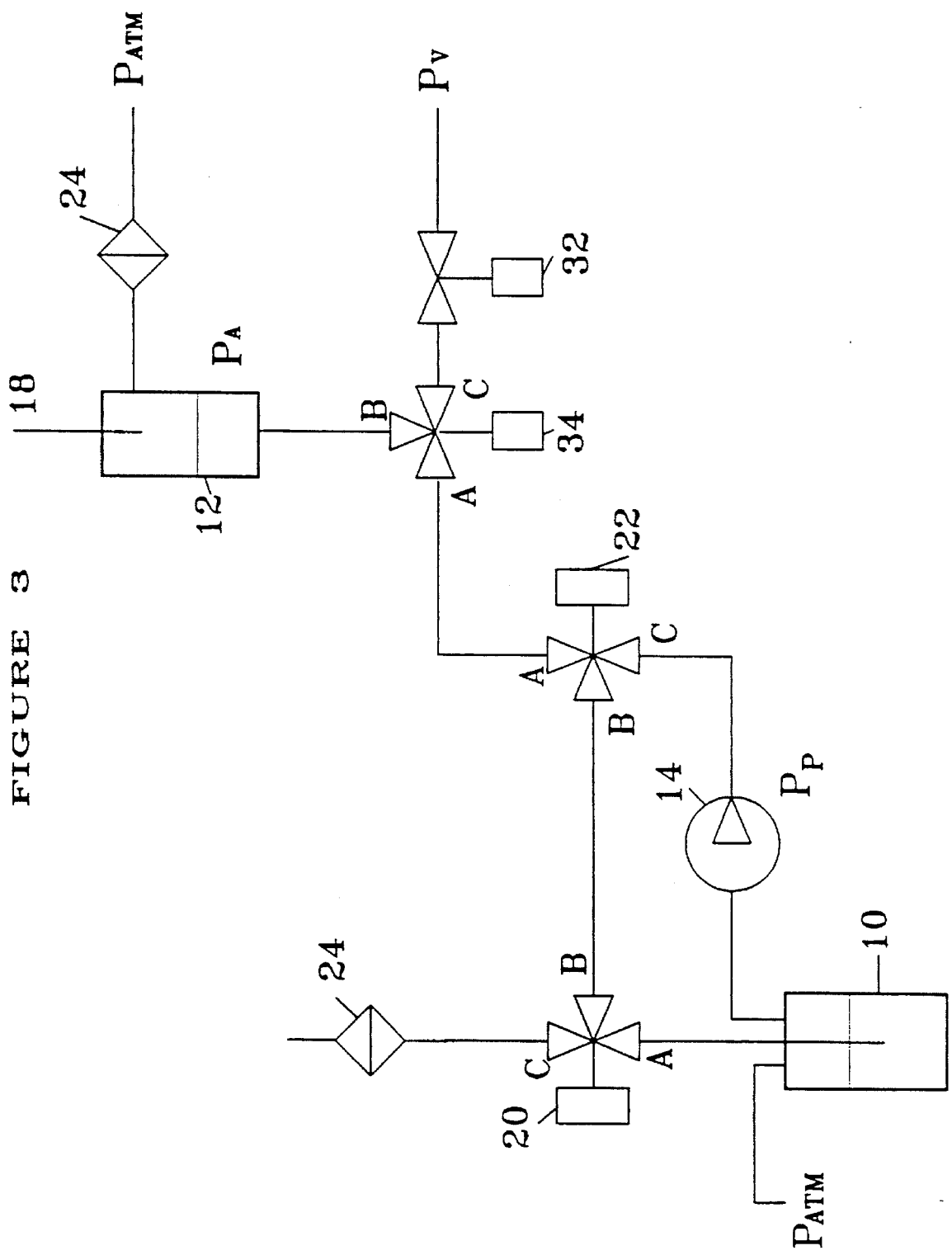
FIG. 3 is a schematic diagram of an alternative embodiment of the system shown in FIG. 2.

In carrying out the invention, according to FIGS. 1–3, the accumulator 12 is filled with the desired amount of liquid sterilant from the reservoir 10, at a first delivery pressure, determined by the difference in the outlet pressure $P_P$ from pump 14 and the pressure of the accumulator $P_A$, and a first delivery rate.

Any other suitable means for creating an absolute pressure differential (corresponding to the first delivery pressure), such that the accumulator 12 is at a lower pressure than the reservoir 10, can also be employed, to move the liquid from the reservoir 10 to the accumulator 12. For instance, a vacuum connected downstream of the accumulator 12 can be used to draw liquid from the reservoir 10. Alternatively, a compressed air head can be used to positively pressurize the reservoir 10, thereby forcing liquid from the reservoir 10 to the accumulator 12.

The amount of liquid delivered to the accumulator 12 is measured in FIG. 1, on a weight basis, by an electronic balance 16 mounted beneath the reservoir 10. The reservoir 10 is preferably fluidly connected to pump 14 is a manner that prevents external forces from acting on the balance 16 during the accumulator 12 fill step.

In FIGS. 2 and 3, the amount of liquid delivered to the accumulator 12 is measured, on a volumetric basis, by a conductivity probe 18 mounted at a predetermined level in the interior of the accumulator 12. When the liquid level reaches the conductivity probe 18, the metering pump stops. The conductivity probe can be adjusted up or down, to accommodate a range of dispense amounts. A vernier with locking set screws can be added to the conductivity probe 18, to facilitate adjustments for different pre-determined dispense amounts. Multiple conductivity probes can be utilized to provide multiple, selectable dispense amounts.

It is also contemplated that the invention can be practiced with other dispensing/measuring means. For example, when a dispensing pump is used to move liquid from the reservoir 10 to the accumulator 12, the amount of liquid metered into the accumulator 12 can be measured by controlling the number of pump strokes of a fixed displacement pump, by controlling the dispensing time period of a continuous flow, fixed output pump, or by controlling the revolution rate of a continuous flow, fixed output pump. When the liquid is moved into the accumulator 12 by creating positive (pressurized reservoir) or negative pressure (evacuated accumulator), metering into the accumulator 12 can be achieved by controlling the time period in which dispensing occurs.

After the desired amount of liquid sterilant has been measured into the accumulator 12, it is discharged or injected into (and through) the vaporizer from the accumulator 12 at a second delivery pressure, determined by the difference in the pressure of the accumulator $P_A$ and the pressure of the vaporizer conduit $P_V$, and a second delivery rate. Any suitable means for creating a pressure differential, corresponding to the second delivery pressure, such that the accumulator 12 is at a higher pressure than the vaporizer, can be used. As described in further detail below, in FIG. 1 positive pressure $P_C$ is applied upstream of the accumulator 12, whereas in FIGS. 2 and 3 a vacuum $P_V$ is applied to the vaporizer conduit.

The first delivery pressure and rate are preferably lower than the second delivery pressure and rate. The first delivery pressure is preferably below 5 psig, and the second delivery pressure is preferably below 120 psig. The first delivery rate is preferably less than ⅓ of the second delivery rate.

Any suitable container for holding and then dispensing the liquid sterilant can be used as the reservoir 10. The reservoir 10, for example, can be a releasable cartridge. The reservoir 10 preferably has a vent of any suitable known variety, which will prevent liquid from spilling out while preventing a buildup of pressure in reservoir 10. Reservoir 10 should be constructed from a material that is storage stable with the liquid sterilant. When aqueous hydrogen peroxide is employed, reservoir 10 is preferably manufactured from high density polyethylene, Kynar, Teflon, polycarbonate, or high purity aluminum. In FIGS. 1–3, the reservoir 10 is vented to atmospheric pressure ($P_{ATM}$).

Any suitable container for accumulating and then discharging the liquid sterilant can be employed as the accumulator 12. While the accumulator 12 need not be constructed from a material which is storage-stable with the liquid sterilant, it should be able to withstand the higher pressures preferably used to discharge the liquid into the vaporizer. The accumulator 12 is preferably manufactured from stainless steel or aluminum. The accumulator 12 is preferably vented to atmospheric pressure ($P_{ATM}$) (controllably in FIG. 1).

Substantially all air bubbles (or other gases or vapors generated by the liquid sterilant) which form in the liquid contained in the reservoir 10 or accumulator 12, during storage or operation, rise to the liquid surface, and become part of the air space above the liquid contained therein.

It is also possible to prevent air bubbles from forming in the dispensing lines upstream of the accumulator 12, during storage or operation, in accordance with the present invention. The embodiments shown in FIGS. 1 and 3 comprise exemplary means for purging substantially all liquid from the dispensing lines upstream of the accumulator 12 with air, after measuring liquid into the accumulator 12, and means for priming these lines with substantially pure liquid, at the beginning of the next measurement pulse. By clearing the dispensing lines of liquid sterilant, the purging step prevents the build-up of air bubbles (or other gases/vapors produced by the liquid sterilant) mixed with liquid in the dispensing equipment, during storage and between measurement pulses. The priming step ensures that the dispensing lines are filled with bubble-free liquid, before sterilant is measured into the accumulator 12. There are substantially no entrained air bubbles to get sucked back into the liquid reservoir 10 and through the dispensing lines, during the priming step. Further, because there are substantially no air bubbles in the dispensing lines, prior to measuring liquid sterilant into the accumulator 12, the measuring accuracy and repeatability is enhanced.

In general, the priming and purging steps are preferably employed when enhanced measuring accuracy is desired. However, the above-described priming and purging steps may not be employed when a conductivity probe 18 mounted in the accumulator is used to meter liquid sterilant from the reservoir 10 to the accumulator 12. Any entrained air bubbles which may have been present in the dispensing lines rise to the surface and enter the air space in the accumulator 12. Thus, the volume of liquid measured by the conductivity probe 18 is substantially free of air bubbles, and is substantially identical each time, regardless of whether or not any air bubbles had formed in the dispensing lines during storage or handling. Yet, when using a very low volume metering pump, to dispense very small quantities of liquid sterilant, or when very high measuring resolutions are desired, the above-described priming and purging steps are preferably employed in connection with a conductivity probe 18, to ensure that measuring accuracy and repeatability are maximized.

The purging and priming steps are carried out in the embodiments shown in FIGS. 1 and 3 by means for flowing liquid sterilant from the reservoir 10 and air from an air source, through the dispensing lines upstream of the accumulator 12 and into a port in the top of the liquid reservoir 10, before and after liquid sterilant is measured into the accumulator 12 from the reservoir 10, respectively. In particular, as described in further detail later herein, the embodiments depicted in FIGS. 1 and 3 comprise a three-way diverter valve 20, which is fluidly connected to a source of air through HEPA air filter 24, the liquid sterilant in the liquid reservoir 10, and the metering pump 14, as well as three-way diverter valve 22, which is fluidly connected to the accumulator 12, the metering pump 14, and a port in the top of the reservoir 10, through a liquid filter 26. Because the length of dispensing line or fluid connection between diverter valve 22 and the accumulator 12 is not subject to the priming and purging steps, diverter valve 22 is preferably placed close to the accumulator 12, to maximize the benefits obtained with the priming and purging steps.

While the invention may be accomplished manually, it is preferably controlled by a suitable microprocessor. The microprocessor may receive input signals, for example, from the measuring means, an internal clock which monitors the progress of the sterilization cycle, pressure sensors, and temperature sensors.

The operation of the invention will now be described in further detail, with reference to FIG. 1. The illustrated system includes a liquid reservoir 10, an accumulator 12, a metering pump 14, an electronic balance 16, three-way diverter valve 20, three-way diverter valve 22, air filter 24, air filter 28, liquid filter 26, two-way valve 30, two-way valve 32, and two-way valve 60.

A compressed air head is connected at $P_C$, while $P_V$ is at or below atmospheric pressure and $P_{ATM}$ is at atmospheric pressure. Air filter 24 is connected to room air. An orifice can be added to valve 30, to restrict the air flow through valve 30 provided by the compressed air head, and thereby prevent splashing in the accumulator 12.

To prime the system, diverter valve 20 is opened through path A-B and diverter valve 22 is opened through path B-C. The metering pump is then energized, creating a suction which slowly draws substantially bubble-free sterilant liquid from the reservoir, through the dispensing lines to diverter valve 22, and back into the reservoir 10. The priming step is continued for a period of time sufficient to fill the primed lines with the liquid.

Next, the pumping is stopped, diverter valve 22 is preferably opened through path B-A, and the initial electronic balance reading recorded. Valve 60 is opened to allow air to escape from the accumulator 12 during the fill step, i.e., $P_A$ equals $P_{ATM}$.

Then, the metering pump 14 is turned back on, so that liquid is slowly withdrawn from the reservoir 10, and passes through diverter valve 20, the metering pump 14, and diverter valve 22, before reaching the accumulator 12. The reading on the electronic balance 16 is monitored, and the weight loss (or amount dispensed to the accumulator) is calculated. When the weight loss equals the amount to be dispensed, the metering pump 14 is stopped, diverter valve 20 is opened through path B-C, and diverter valve 22 is opened through path B-C.

The metering pump 14 is then energized again, so that it pumps filtered air through air filter 24, diverter valve 20, diverter valve 22, and into the air space above the liquid remaining in the reservoir 10. The air flow purges substantially all liquid from its flow path.

Next, two-way valve 30 is opened to pressurize the space above the liquid in the accumulator 12 to pressure $P_C$, i.e., $P_A$ now equals the pressure of the compressed air supply. Two-way valve 32 is opened, and the liquid in the accumulator 12 is discharged quickly by the pressure differential $P_A$-$P_V$, through two-way valve 32.

Table I reports data obtained by metering various amounts of a 30–35% hydrogen peroxide solution, using the same apparatus, configured as depicted in FIG. 1. The maximum capacity of the accumulator 12 for the hydrogen peroxide solution was 400 g.

TABLE I

| Selected Dispense Amounts (grams) | Actual Average | Dispense Amounts (grams) Minimum | Maximum | Number of Tests |
|---|---|---|---|---|
| 4 | 4.3 | 4.1 | 4.5 | 4 |
| 28 | 28.08 | 27.7 | 28.3 | 25 |

TABLE I-continued

| Selected Dispense Amounts (grams) | Actual Average | Dispense Amounts (grams) Minimum | Maximum | Number of Tests |
|---|---|---|---|---|
| 42 | 42.21 | 42.0 | 42.0 | 10 |
| 49.6 | 49.80 | 49.7 | 49.9 | 7 |
| 56 | 55.97 | 55.5 | 56.3 | 10 |
| 200 | 200.23 | 200.1 | 200.4 | 3 |
| 400 | 400.3 | — | — | 1 |
| 8 | 8.35 | 8.0 | 8.7 | 12 |
| 20 | 20.24 | 19.9 | 20.5 | 12 |
| 30 | 30.125 | 30.0 | 30.3 | 8 |
| 40 | 40.18 | 40.0 | 40.4 | 6 |
| 50 | 50.1275 | 50.1 | 50.4 | 8 |
| 60 | 60.1875 | 60.1 | 60.3 | 8 |
| 70 | 70.225 | 70.1 | 70.3 | 8 |
| 80 | 80.28 | 80.2 | 80.3 | 6 |
| 90 | 90.325 | 90.1 | 90.5 | 8 |
| 100 | 100.2 | 100.1 | 100.3 | 8 |

The apparatus was controlled by a microprocessor, which interfaced with a user touchpad. The microprocessor received an input signal from the balance 14 and was pre-programmed with the desired or selected dispense amounts, reported in the left hand column of Table I. When different dispense amounts were entered into the touchpad, the microprocessor automatically adjusted the amount of liquid sterilant dispensed.

During accumulator fill, the pump pressure $P_p$ ranged from 0.5 to about than 5 psig, while $P_A$ equaled atmospheric pressure. Thus, the first delivery pressure ranged between about 0.5 to 5 psig. Pressure $P_C$ (=$P_A$ during the accumulator discharge) ranged from 80–90 psig, while pressure $P_V$ was at 1 Torr absolute vacuum. Thus, the second delivery pressure ranged from about 95–105 psig.

The first delivery time, or time to fill the accumulator 12 ranged from about 15 sec to about 14 minutes, depending on the dispense amount. The time during which the accumulator 12 was discharged ranged from less than about 1 sec to about 30 sec.

As demonstrated in Table I, the metering accuracy was virtually equal over a 100:1 range of dispense amounts, using the same mechanical hardware.

The rate at which the accumulator 12 was filled was varied depending upon the remaining amount to be dispensed. A higher fill rate was employed until approximately 25 g remained to be dispensed. Then, a lower fill rate was employed.

The operation of the invention will now be further described with reference to FIG. 2, where the depicted embodiment includes a vented reservoir 10, an accumulator 12, a metering pump 14, conductivity probe 18, three-way valve 34, air filter 24, and two-way valve 32. A vacuum equal to $P_V$ is applied at the vaporizer (not shown) conduit and the accumulator is at atmospheric pressure $P_{ATM}$. The conductivity probe 18 is positioned at a level inside the accumulator 12, such that when the desired amount of liquid is delivered into the accumulator 12, the liquid level reaches the conductivity probe 18.

Three-way valve 34 is opened through path A-B. The metering pump 14 is started, creating a pressure differential $P_P$-$P_A$, which slowly draws liquid sterilant from the reservoir 10 into the accumulator 12. When the liquid level in the accumulator 12 reaches the conductivity probe 18, the metering pump 14 is stopped. Substantially all air bubbles which may have been in the dispense lines upstream of the accumulator 12 rise to the air space in the accumulator 12 (and subsequently escape into the atmosphere). Thus, virtually identical amounts of liquid are measured repeatedly into the accumulator 12, despite the presence of any air bubbles.

Next, three-way valve 34 is opened through path B-C, and two-way valve 32 is opened. The liquid in the accumulator 12 is discharged quickly by the pressure differential $P_A$-$P_V$, through three-way valve 34 and two-way valve 32.

Table 2 reports data obtained by metering various amounts of a 30–35% hydrogen peroxide solution, using the same apparatus, configured as depicted in FIG. 2. The maximum capacity of the accumulator 12 for the solution was about 7 grams. The conductivity probe 18 could be mechanically adjusted up and down, to accommodate a 10:1 range of dispense amounts. Table 2 contains data for four positions of the conductivity probe 18.

TABLE 2

| Actual Average | Dispense Amounts (grams) Minimum | Maximum | Number of Tests |
|---|---|---|---|
| 0.507 | 0.49 | 0.53 | 30 |
| 1.803 | 1.78 | 1.81 | 30 |
| 3.265 | 3.25 | 3.29 | 30 |
| 5.785 | 5.76 | 5.79 | 20 |

The first delivery pressure ($P_P$-$P_A$) equaled about ½ psig. $P_V$ was at 200 microns of vacuum. Thus, the second delivery pressure ($P_A$-$P_V$) was about 14½ psig.

The first delivery time, or time to fill the accumulator ranged from about 10 seconds to about 100 seconds, depending on the dispense amount. The liquid was typically discharged from the accumulator 12 in about 1½ to 15 seconds.

FIG. 3 is an alternative embodiment of the system shown in FIG. 2, which can be used when metering very small quantities of sterilant, to maximize measuring accuracy. In addition to the components depicted in FIG. 2, the system of FIG. 3 includes the means for purging and priming the dispensing lines upstream of the accumulator, shown in FIG. 1 and previously described herein.

In particular, the system of FIG. 3 also includes three-way diverter valve 20, three-way diverter valve 22, and a second air filter 24, which is connected to room air.

Figure 4:
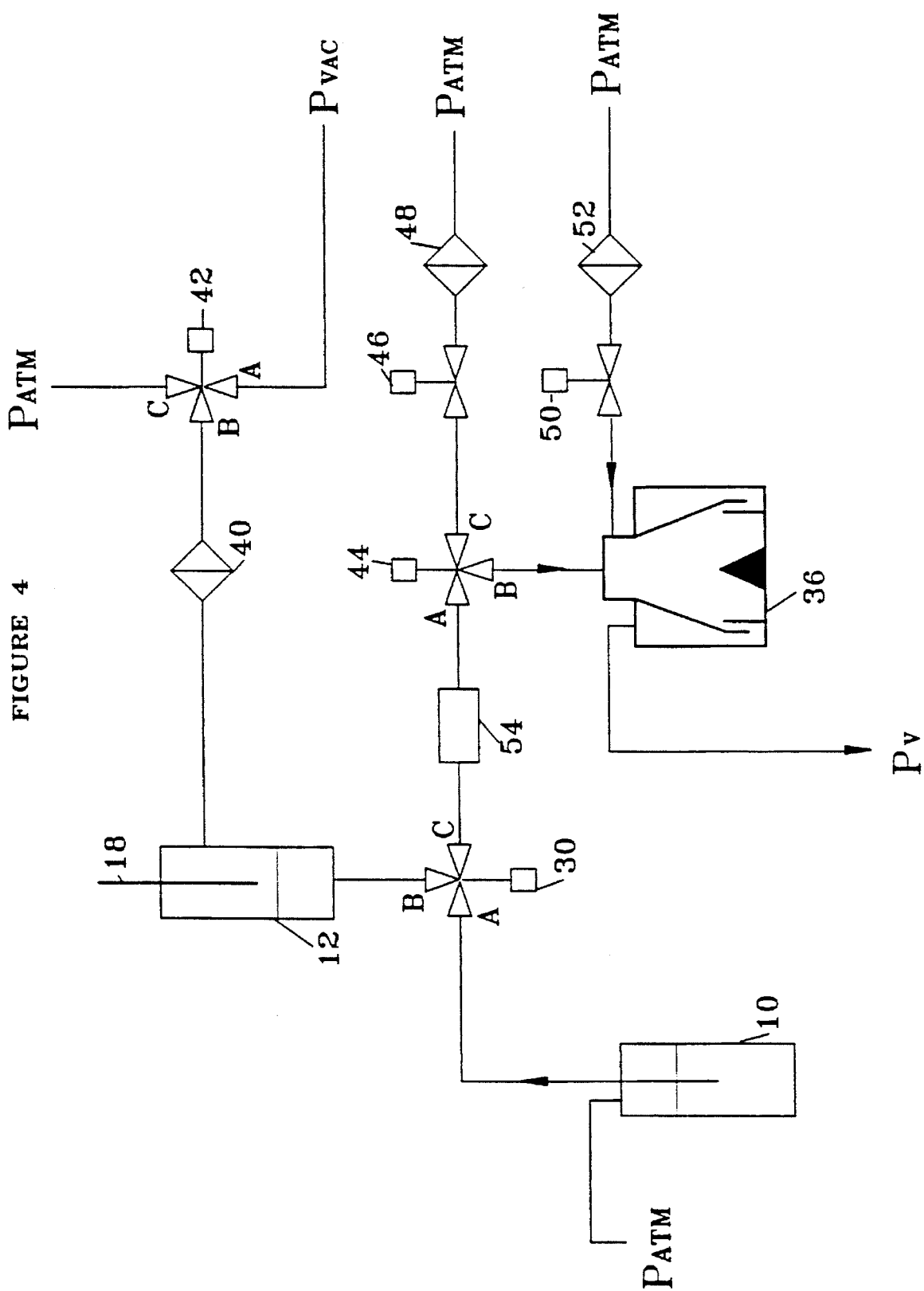
FIG. 4 is a schematic diagram of another embodiment of a system for practicing the method of the present invention, wherein the accumulator is coupled to a vaporizer capable of either vacuum or flow-through operation.

FIG. 4 illustrates a further embodiment of the invention, which includes a reservoir 10, an accumulator 12, a conductivity probe 18, a vaporizer 36, a three-way valve 30, a hydrophobic filter 40, a three-way valve 42, a three-way valve 44, a two-way valve 46, an air filter 48, a two-way air break valve 50, an air filter 52, and an air bubble conductivity detector 54.

In FIG. 4, a vacuum source, rather than a metering pump, is used to fill the accumulator 12, by creating a pressure differential ($P_{ATM}$-$P_{VAC}$) corresponding to the first delivery pressure) between the reservoir 10 and the accumulator 12. The vacuum source ($P_{VAC}$) is connected upstream of path A-B through three-way valve 42. Reservoir 10 is vented to room air ($P_{ATM}$).

As in FIGS. 1–3, a pressure differential ($P_V$-$P_{ATM}$), corresponding to the second delivery pressure, is created to discharge liquid from the accumulator 12 into the vaporizer 36. In FIG. 4, the pressure differential is created by placing a vacuum at $P_V$, downstream of the vaporizer 36, and through the sterilization chamber (not shown). The lines upstream of air filters 48 and 52 are placed at atmospheric pressure, connected to room air at $P_{ATM}$. The accumulator 12, through path B-C in three-way valve 42, is controllably vented to room air (during accumulator discharge).

The system shown in FIG. 4 is equipped to meter sterilant into and through the vaporizer 36 to the sterilization chamber under a combination of deep vacuum and flow-through conditions, in one sterilization cycle. The combination vacuum/flow-through method is disclosed in commonly assigned, copending application U.S. Ser. No. 851,415, entitled "Sterilization Apparatus and Method for Multicomponent Sterilant," filed on Mar. 13, 1992, and incorporated by reference herein. The operating pressures within the accumulator 12, vaporizer 36, chamber (not shown) and associated accumulator discharge piping can be at virtually any value up to 120 psig. This permits deep vacuum pulses combined with vacuum (or pressure) flow-through periods, and allows the method to be utilized for the sterilization/decontamination of compressed air tools as well as endoscopes, for example.

An accumulator fill precedes each deep vacuum pulse and/or each flow-through period. Valve 44 and valve 46 are pulsed, as required, as the contents of the accumulator 12 are discharged at the desired second delivery rate into the vaporizer 36.

A vacuum flow-through period is accomplished as follows using the apparatus in FIG. 4. To deliver liquid sterilant from the reservoir 10 into the accumulator 12, three-way valve 30 is opened through path A-B, and three-way valve 42 is opened through path B-A. Liquid is slowly drawn into the accumulator 12, by the pressure differential $(P_{ATM}-P_{VAC})$ created between the accumulator 12 and the reservoir 10, i.e., the reservoir 10 is at $P_{ATM}$, and the accumulator 12 is at $P_{VAC}$.

When the liquid level in the accumulator 12 reaches the conductivity probe 18, three-way valve 30 is opened through path B-C, and three-way valve 42 is opened through path B-C.

Valves 44 and 46 are controllably pulsed to that the liquid in the accumulator 12 is then quickly discharged through the accumulator 12 and into the vaporizer, by the pressure differential $P_{ATM}-P_V$, i.e., the accumulator 12 is at $P_{ATM}$ and the vaporizer conduit is at $P_V$.

During discharge of liquid from the accumulator 12, three-way valve 44 is pulsed continuously, along with valve 46 so that discrete increments of liquid, approximating a steady stream, pass through path A-B of valve 44. Room air is alternatively drawn through air filter 48 and air injector valve 46 through path C-B of three-way valve 44. Room air is simultaneously drawn through air filter 52 and air break valve 50 into the fluid path from valve 44 through the vaporizer 36 and to the sterilization chamber by the pressure differential between $P_{ATM}$ and the vaporizer 36.

An air restriction, such as a venturi, is preferably utilized where the liquid from path A-B through valve 44 combines in the vaporizer 36 with the air flow through valve 50. This controls the sterilant concentration during flow through.

In FIG. 4, bubble conductivity detector 54 can be used to detect the absence or presence of liquid in the dispense line connecting the accumulator 12 to the vaporizer 36. This assures that the accumulator 12 has been discharged completely.

The embodiment shown in FIG. 4 can be operated at positive flow-through pressure, if the valves 42, 46, and 50 are connected to a positive pressure, compressed air source at pressure $P_c$ in lieu of atmospheric pressure.

Figure 5:
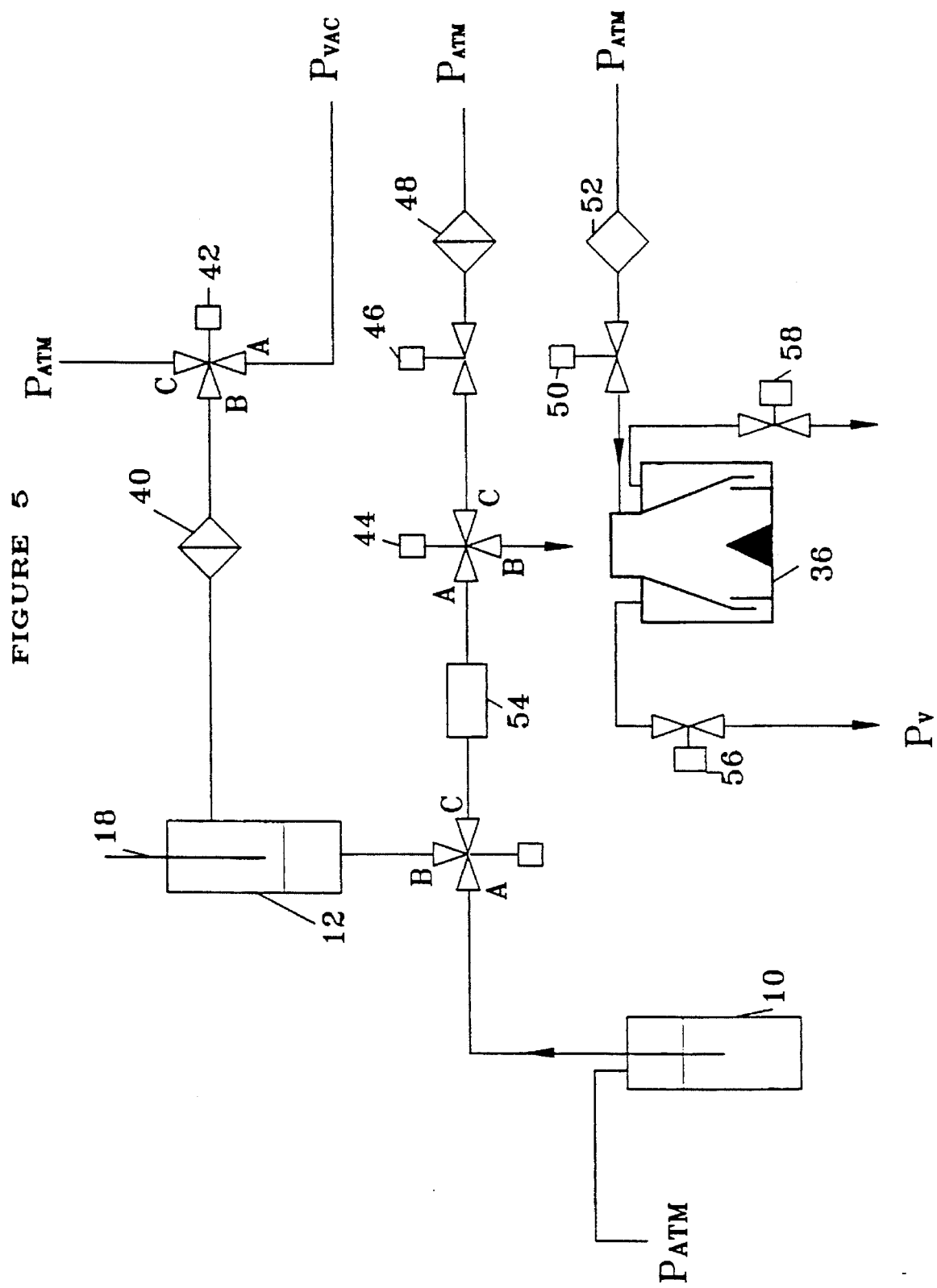
FIG. 5 is a schematic diagram of an alternative embodiment of the system shown in FIG. 4, wherein the vaporizer is connected to an exhaust for purging the system of excess sterilant.

The embodiment shown in FIG. 5 includes all the components of the system of FIG. 4, and also includes two-way valve 56, fluidly connected between the vaporizer 36 and sterilization chamber, and two-way valve 58, fluidly connected in parallel with the sterilization chamber, between the vaporizer 36 and downstream vacuum. When valve 56 is closed and valve 58 is opened, excess liquid in the accumulator 12 and downstream thereof (such as may be present at the end of the day) can be exhausted from the system through the vaporizer 36 and valve 58. This embodiment can be utilized by service technicians, prior to servicing any components containing liquid sterilant.

While the invention is susceptible to various modifications and alternative forms, the preferred embodiments have been described herein in detail. It is to be understood, however, that it is not intended to limit the invention to the specific forms disclosed. On the contrary, it is intended to cover all modifications and alternative forms falling within the spirit and scope of the invention.

What is claimed is:

1. A method of metering a degradative liquid sterilant from a container into a vaporizer, which comprises the steps of:
   a) delivering a predetermined amount of degradative liquid sterilant from a container into a vented accumulator, at a first delivery pressure and a first delivery rate, wherein the container and the accumulator are fluidly connected;
   b) discontinuing the delivery of liquid sterilant when the predetermined amount of sterilant has been transferred from the container into the accumulator, wherein said predetermined amount can be selected from a range of predetermined amounts which can be less than the volume of the accumulator; and
   c) substantially completely discharging the liquid sterilant contained in the accumulator into the vaporizer, at a second delivery pressure and a second delivery rate, wherein the accumulator and the vaporizer are fluidly connected;

wherein the first delivery rate is lower than the second delivery rate and wherein the first delivery pressure is lower than the second delivery pressure.

2. The method of claim 1, wherein step (a) comprises creating an absolute pressure differential between the container and the accumulator, which corresponds to the first delivery pressure, wherein the container is at a higher pressure than the accumulator.

3. The method of claim 2, which further comprises pumping liquid sterilant from the container into the accumulator, with pumping means.

4. The method of claim 3, wherein the pumping means comprises a fixed displacement, metering pump.

5. The method of claim 4, wherein the pumping means comprises a peristaltic tubing pump.

6. The method of claim 1, wherein step (c) comprises creating an absolute pressure differential between the accumulator and the vaporizer, which corresponds to the second delivery pressure, wherein the accumulator is at a higher pressure than the vaporizer.

7. The method of claim 1, wherein the first delivery pressure is below about 5 psig and the second delivery pressure is below about 120 psig.

8. The method of claim 1, wherein the first delivery rate is less than about one-fifth of the second delivery rate.

9. The method of claim 1, wherein step (b) comprises measuring the amount of liquid sterilant delivered from the container into the accumulator.

10. The method of claim 9, which comprises weighing the amount of liquid sterilant delivered from the container into the accumulator.

11. The method of claim 9, which comprises determining the volume of liquid sterilant delivered from the container into the accumulator.

12. The method of claim 1, which further comprises the step of flowing air from an air source through a portion of the fluid connection between the container and the accumulator and into a port in the container, after step (c).

13. The method of claim 1, which further comprises the step of flowing liquid sterilant from the container through a portion of the fluid connection between the container and the accumulator and back into a port in the container, prior to step (a).

14. The method of claim 1, wherein the liquid sterilant is delivered from the accumulator into the vaporizer through a controllable, pulsating valve member.

15. The method of claim 14, wherein there is more than about one minute between pulses.

16. The method of claim 1, wherein the liquid sterilant generates gas or vapor during storage or operation.

17. The method of claim 15, wherein the liquid sterilant comprises hydrogen peroxide.

18. A system for metering a degradative liquid sterilant from a container into a vaporizer for vapor phase sterilization, which comprises:

a) a container for liquid sterilant;
  b) a vented accumulator for receiving liquid sterilant from the container, which is fluidly coupled to the container;
  c) a vaporizer for vaporizing the liquid sterilant, which is fluidly connected to the accumulator;
  d) means for measuring a predetermined amount of liquid sterilant to be delivered from the container into the accumulator, wherein said predetermined amount can be selected from a range of predetermined amounts which can be less than the volume of the accumulator;
  e) first delivery means for delivering the predetermined amount of liquid sterilant from the container into the accumulator at a first delivery rate; and
  f) second delivery means for substantially completely discharging the liquid sterilant contained in the accumulator into the vaporizer at a second delivery rate which is higher than the first delivery rate and at a second pressure which is higher than the first delivery pressure.

19. The system of claim 18, wherein the first delivery means comprises means for creating an absolute pressure differential between the container and the accumulator, wherein the container is at a higher pressure than the accumulator.

20. The system of claim 19, wherein the first delivery means comprises pumping means.

21. The system of claim 20, wherein the pumping means comprises a fixed displacement metering pump.

22. The system of claim 21, wherein the pumping means comprises a peristaltic tubing pump.

23. The system of claim 18, wherein the second delivery means comprises means for creating an absolute pressure differential between the accumulator and vaporizer, wherein the accumulator is at a higher pressure than the vaporizer.

24. The system of claim 18, wherein the measuring means comprises a balance positioned beneath the container.

25. The system of claim 18, wherein the measuring means comprises means for measuring the volume of liquid delivered from the container into the accumulator.

26. The system of claim 18, wherein the measuring means comprises a conductivity probe.

27. The system of claim 18, which further comprises means for flowing air from an air source through a portion of the fluid connection between the container and the accumulator and into a port in the container, and means for flowing liquid sterilant from the container through a portion of the fluid connection between the container and the accumulator and back into a port in the container.

28. The system of claim 26, which further comprises first and second three-way valves disposed between the container and the accumulator, wherein the first valve is fluidly connected to a source of air and is adjacent to the container, and the second valve is fluidly connected to a port in the container and is adjacent to the accumulator.

29. The system of claim 18, further comprising a controllable, pulsing valve member disposed between the accumulator and the vaporizer.

30. The system of claim 18, further comprising a sterilization chamber, which is fluidly connected to the vaporizer.

31. The system of claim 29, further comprising an air path through the vaporizer and the fluid connection between the sterilization chamber and the vaporizer.

32. The system of claim 18 wherein the vaporizer comprises a sterilization chamber.

* * * * *